US011534400B2

(12) United States Patent
Labbe et al.

(10) Patent No.: US 11,534,400 B2
(45) Date of Patent: Dec. 27, 2022

(54) COMPOSITIONS AND METHODS FOR IMPROVING HYDRATION OF INDIVIDUALS HAVING DYSPHAGIA

(71) Applicant: NESTEC S.A., Vevey (CH)

(72) Inventors: David Philippe Labbe, Lausanne (CH); Julie Ann Swanson, Minneapolis, MN (US); Adam Burbidge, Arzier (CH)

(73) Assignee: Societe des Produits Nestle S.A., Vevey (CH)

( * ) Notice: Subject to any disclaimer, the term of this patent is extended or adjusted under 35 U.S.C. 154(b) by 247 days.

(21) Appl. No.: 16/305,422

(22) PCT Filed: Jun. 2, 2017

(86) PCT No.: PCT/EP2017/063413
§ 371 (c)(1),
(2) Date: Nov. 29, 2018

(87) PCT Pub. No.: WO2017/207743
PCT Pub. Date: Dec. 7, 2017

(65) Prior Publication Data
US 2020/0323774 A1 Oct. 15, 2020

Related U.S. Application Data

(60) Provisional application No. 62/345,363, filed on Jun. 3, 2016.

(51) Int. Cl.
*A61K 9/00* (2006.01)
*A61K 31/19* (2006.01)
*A61K 31/16* (2006.01)
*A23L 2/395* (2006.01)
*A23L 2/68* (2006.01)

(52) U.S. Cl.
CPC ............ *A61K 9/0095* (2013.01); *A23L 2/395* (2013.01); *A23L 2/68* (2013.01); *A61K 9/0056* (2013.01); *A61K 31/16* (2013.01); *A61K 31/19* (2013.01)

(58) Field of Classification Search
CPC ....... A61K 9/0095; A61K 31/16; A61K 31/19
See application file for complete search history.

(56) References Cited

U.S. PATENT DOCUMENTS

| | | | |
|---|---|---|---|
| 2004/0191388 A1* | 9/2004 | Rifkin | A23L 2/38 426/590 |
| 2006/0204551 A1* | 9/2006 | Manley | A23L 27/14 424/439 |
| 2010/0285178 A1* | 11/2010 | Labbe | A23L 27/105 426/66 |
| 2011/0195042 A1 | 8/2011 | Huetter et al. | |
| 2012/0046641 A1* | 2/2012 | Jedwab | A61B 5/14539 604/503 |

FOREIGN PATENT DOCUMENTS

| | | |
|---|---|---|
| CN | 102209472 A | 10/2011 |
| JP | 2015530412 A | 10/2015 |
| WO | 2007125888 A1 | 11/2007 |
| WO | 2009063005 | 5/2009 |
| WO | 2010082986 | 7/2010 |

OTHER PUBLICATIONS

The Merriam-Webster Online Dictionary definition of "derivative". Downloaded Oct. 26, 2018 from: https://www.merriam-webster.com/dictionary/derivative (Year: 2018).*
Google patent search_Aug. 12, 2020 (Year: 2020).*
Google scholar search_Aug. 12, 2020 (Year: 2020).*
T. Ebihara, et al. "Effects of menthol on the triggering of the swallowing reflex in elderly patients with dysphagia," Br. J. Clin. Pharmacol. 2006, 62:3, 369-371. (Year: 2006).*
Product Information document for ThickenUP Clear, downloaded May 28, 2021 from https://www.nestlenutritionstore.com/resource-thickenup-clear.html (Year: 2021).*
C.M. Steele. "Mapping Bracco's Varibar® barium products to the IDDSI Framework," downloaded May 28, 2021 from https://iddsi.org/IDDSI/media/images/Publications/Mapping-Varibar-to-IDDSI-Framework.pdf. (Year: 2017).*
Beverage with salivation agent—Google Search—May 26, 2021 (Year: 2021).*
Ebihara et al. "Effects of menthol on the triggering of the swallowing reflex in elderly patients with dysphagia" British Journal of Clinical Pharmacology, 2006, vol. 62, No. 3, pp. 369-371.
Sugiyama et al. "A Novel Animal Model of Dysphagia Following Stroke" Dysphagia, 2014, vol. 29, pp. 61-67.
Kawada et al., "Clinical Evaluation of a Moisturizing Spray for Xerostomia", Dental Therapy, vol. 32, Issue No. 1, 2013, pp. 10-15.
Japan Patent Office Action Received for Applicaion No. 2018-560867, Dispatch No. 168521, Dispatch Date Apr. 21, 2021, 14 Pages.
Chen et al., "Principle of Food Chemistry", South China University of Technology Press, Feb. 28, 2015, p. 417.

(Continued)

*Primary Examiner* — Michael P Cohen
(74) *Attorney, Agent, or Firm* — K&L Gates LLP

(57) ABSTRACT

A method of treating or preventing dehydration in an individual having impaired swallowing such as dysphagia can include administering to the individual having the dysphagia an effective amount of a composition containing a salivating agent and a cooling agent in a weight ratio of 1:0.06 to 1:0.2. Optionally the composition includes a tingling agent. The composition can be a powder that is reconstituted before administration, for example at the point of consumption. A thickening or thin cohesive agent can be included in the powder and/or can be included in a liquid in which the powder is reconstituted. The composition can be a beverage containing the salivating agent and the cooling agent in a total amount of at least 3.0 wt. % of the beverage, for example at least 6.0 wt. % of the beverage. The composition can be a ready-to-drink beverage or a frozen dessert on a stick.

18 Claims, No Drawings

(56) References Cited

OTHER PUBLICATIONS

Ning, "Food Biochemistry", South China University of Technology Press, Jul. 31, 2006, pp. 365-368.
China Office Action Received for Application No. 201780028210.3, dated Dec. 31, 2020, 20 pages.
Journal of the Japanese Society of Cooking Science, vol. 46, Issue No. 1, 2013, pp. 1-7.
Japan Patent Office Communication for Application No. P2018-560867, Dispatch No. 816540, Dispatch Date Nov. 30, 2021, 10 Pages.
Li et al., "Comprehensive Rehabilitation for Improving Dysphagia and Ptyalism in Patints with Stroke", Chinese Journal of Clinical Rehabilitation, Issue No. 22, Oct. 5, 2005, pp. 4401-4403.
Liu et al., "Effect of Acid and Cold Stimulation on Dysphagia After Stroke", Chinese Journal of Urban and Rural Industrial Hygiene, Issue No. 06, Dec. 15, 2013, pp. 35-36.
Yang et al., "Effect of Community Rehabilitation Guidance in Combination with Cold Stimulation on Dysphagia After Cerebral Infarction", Chronic Pathematology Journal, vol. 16, Issue No. 4, Jul. 15, 2015, pp. 443-444.
China Patent Office Communication for Application No. 202210121132.4, dated Aug. 31, 2022, 10 pages.

\* cited by examiner

COMPOSITIONS AND METHODS FOR IMPROVING HYDRATION OF INDIVIDUALS HAVING DYSPHAGIA

CROSS REFERENCE TO RELATED APPLICATIONS

The present application is a National Stage of International Application No. PCT/EP2017/063413, filed on Jun. 2, 2017, which claims priority to U.S. Provisional Patent Application No. 62/345,363, filed on Jun. 3, 2016, the entire contents of which are being incorporated herein by reference.

BACKGROUND

The present disclosure generally relates to compositions and methods for improving hydration of individuals having impaired swallowing such as dysphagia. More specifically, the present disclosure relates to administering a composition comprising a salivating agent, a cooling agent and optionally a tingling agent to an individual having dysphagia.

Dysphagia is characterized by impaired involuntary motor control of swallowing process and can cause "penetration" which is the entry of foreign material into the airway. The airway invasion can be accompanied by "aspiration" in which the foreign material enters the lungs and can lead to serious health risks. Epidemiological studies estimate a prevalence rate of dysphagia of 16% to 22% among individuals over fifty years of age.

Esophageal dysphagia affects a large number of individuals of all ages, but is generally treatable with medications and is considered a less serious form of dysphagia. Esophageal dysphagia is often a consequence of mucosal, mediastinal, or neuromuscular diseases. Mucosal (intrinsic) diseases narrow the lumen through inflammation, fibrosis, or neoplasia. Mediastinal (extrinsic) diseases obstruct the esophagus by direct invasion or through lymph node enlargement. Neuromuscular diseases may affect the esophageal smooth muscle and its innervation by disrupting peristalsis and/or lower esophageal sphincter relaxation.

On the other hand, oral pharyngeal dysphagia is a very serious condition and is generally not treatable with medication. Oral pharyngeal dysphagia also affects individuals of all ages but is more prevalent in older individuals. Worldwide, oral pharyngeal dysphagia affects approximately 22 million people over the age of fifty. Oral pharyngeal dysphagia is often a consequence of an acute event, such as a stroke, brain injury, or surgery for oral or throat cancer. In addition, radiotherapy and chemotherapy may weaken the muscles and degrade the nerves associated with the physiology and nervous innervation of the swallow reflex. Individuals with progressive neuromuscular diseases such as Parkinson's disease also may experience increasing difficulty in swallow initiation.

Dysphagia has major consequences on patient health and healthcare costs. Individuals with more severe dysphagia generally experience a sensation of impaired passage of food from the mouth to the stomach, occurring immediately after swallowing. Among community-dwelling individuals, perceived symptoms may prompt patients to see a doctor. Among institutionalized individuals, health care practitioners may observe symptoms or hear comments from the patient or a family member suggestive of swallowing impairment and recommend the patient be evaluated by a specialist.

Severity of dysphagia may vary from: (i) minimal (perceived) difficulty in safely swallowing foods and liquids, (ii) an inability to swallow without significant risk for aspiration or choking, and (iii) a complete inability to swallow. Commonly, the inability to properly swallow foods and liquids may be due to food boluses being broken up into smaller fragments, which may enter the airway or leave unwanted residues in the oropharyngeal and/or esophageal tract during the swallowing process (e.g., aspiration). If enough material enters the lungs, the patient may drown on the food/liquid that has built up in the lungs. Even small volumes of aspirated food may lead to bronchopneumonia infection, and chronic aspiration may lead to bronchiectasis and may cause some cases of asthma.

"Silent aspiration," a common condition among elderly, refers to the aspiration of the oropharyngeal contents during sleep. People may compensate for less-severe swallowing impairments by self-limiting the diet. The aging process itself, coupled with chronic diseases such as hypertension or osteoarthritis, predisposes elderly to (subclinical) dysphagia that may go undiagnosed and untreated until a clinical complication occurs.

The economic costs of dysphagia are associated with hospitalization, re-hospitalization, loss of reimbursement due to pay for performance ("P4P"), infections, rehabilitation, loss of work time, clinic visits, use of pharmaceuticals, labor, care taker time, childcare costs, quality of life, and increased need for skilled care. Dysphagia and aspiration impact quality of life, morbidity and mortality. Twelve-month mortality is high (45%) among individuals in institutional care who have dysphagia and aspiration. The economic burden of the clinical consequences arising from failure to manage dysphagia is significant.

SUMMARY

A study of older persons with dysphagia identified that all had inadequate fluid intake. Patients with impaired swallowing such as dysphagia are at particular risk for dehydration due to insufficient consumption of fluids, especially thickened fluids. Increasing fluid thickness is associated with a decrease in intake as compared to daily fluid intake goals (Cichero 2013). With conventional care, 39% of dysphagia patients are likely to be dehydrated (Botella 2002).

Dysphagia-related dehydration has a clinical and economic burden. Individuals with swallowing difficulties are at higher risk for dehydration (inadequate intake) and fluid or electrolyte imbalance. According to Botella et al. (2002), the incidence of dehydration in dysphagic patients is 39%, leading to almost 20 million dysphagic patients suffering from dehydration in Europe and almost 10 million in the U.S. According to U.S. hospitalization data from 2002, there were 2,531,000 hospitalizations related to dehydration, and the mortality rate from a dehydration diagnosis is estimated to be 2.9%. Thus, based on the prevalence of dysphagic patients in the U.S., it can be estimated that almost 280,000 deaths were related to dysphagic dehydration, and almost 580,000 deaths in Europe (assuming similar dehydration mortality rate). Dehydration also increases hospital mortality by two-fold in patient admitted with stroke, doubles the risk of pressure ulcers, and increases hospital length of stay in patients with community acquired pneumonia (Thomas 2004).

In addition, the economic cost of dehydration is significant. In the U.S., dehydration was associated with an average hospital cost of $9.1 billion in 2002 (HCUP 2002).

The present inventors recognized that dysphagic patients typically do not drink a sufficient amount. This can be attributed to various factors, not least of which is the unnatural experience of drinking thickened fluids, which are not perceived as very refreshing in the same way as a typical glass of cold water. Consequently, patients with dysphagia have a high risk of dehydration, and the incidence of dehydration associated with dysphagia is near 32%, creating significant problems:

Inadequate fluid intake predisposes frail elderly to clinical complications that increase healthcare utilization and the threat of death.

Dehydration as the principal diagnosis is associated with a mean length of hospital stay over 4 days and over $7,000 in costs for hospital care.

Among individuals hospitalized for pneumonia, the presence of dehydration increases hospital mortality by 100%.

Dehydration among stroke patients with dysphagia is associated with increased mortality at 3 months.

Without wishing to be bound by theory, the present inventors believe that a refreshing, thirst quenching solution that stimulates swallowing and salivation and increases fluid intake can avoid dehydration in a dysphagic patient and/or treat dysphagia.

Accordingly, in a general embodiment, the present disclosure provides a method of treating or preventing dehydration in an individual having impaired swallowing, the method comprising administering to the individual an effective amount of a composition comprising a salivating agent and a cooling agent. More preferably, the invention provides a method comprising administering to an individual having dysphagia an effective amount of a composition comprising a salivating agent and a cooling agent in a weight ratio of 1:0.06 to 1:0.2.

In an embodiment, the salivating agent is one or more organic acids selected from the group consisting of adipic, ascorbic, citric, fumaric, lactic, malic and tartaric acids.

In an embodiment, the cooling agent is selected from the group consisting of menthol derivative compounds, acyclic carboxamides, cyclic carboxamides, N-substituted paramenthane carboxamides, phosphine oxides, substituted p-menthanes, menthoxypropane, alpha-keto enamine derivatives, N-substituted p-menthane carboxamide, menthyl half acid ester derivatives, cubebol and mixtures thereof.

In an embodiment, the composition further comprises a tingling agent. The tingling agent can be selected from the group consisting of spilanthol, saanshool-I, saanshool-II, sanshoamide, chavicine, piperine, *Echinacea* extract, Northern Prickly Ash extract, red pepper oleoresin, and mixtures thereof.

In an embodiment, the composition comprises a thickening or thin cohesive agent. The thickening agent can be selected from the group consisting of xanthan gum, guar gum (e.g., partially hydrolyzed guar gum), carrageenan, native starch, modified starch, and mixtures thereof.

In an embodiment, the composition is administered to the individual at least once a day for at least one week.

In an embodiment, the composition is a beverage comprising the salivating agent and the cooling agent in a total amount of at least 3.0 wt. % of the beverage, and in some embodiments at least 6.0 wt. % of the beverage. The beverage can have a nectar-like viscosity, for example 35-350 cP (e.g., 50-170 cP), or can have a viscosity greater than 1,750 cP. In some embodiments, the beverage may be classified as Slightly Thick, Mildly Thick, Moderately Thick or Extremely thick according to the International Dysphagia Diet Standardization Initiative (IDDSI) criteria (September 2015).

In an embodiment, the beverage is a thin cohesive liquid as disclosed in U.S. Patent App. Pub. No. 2015/0004149, incorporated herein by reference in its entirety. For example, the beverage can comprise a food grade biopolymer selected from the group consisting of botanical hydrocolloids, microbial hydrocolloids, animal hydrocolloids, algae hydrocolloids and combinations thereof. Non-limiting examples of suitable algae hydrocolloids include agar, carrageenan, alginate, and combinations thereof. Non-limiting examples of suitable microbial hydrocolloids are selected from the group consisting of xanthan gum, gellan gum, curdlan gum, and combinations thereof. Non-limiting examples of suitable botanical hydrocolloids include plant-extracted gums, plant-derived mucilages, and combinations thereof. Non-limiting examples of suitable plant-extracted gums include okra gum, konjac mannan, tara gum, locust bean gum, guar gum (e.g., partially hydrolyzed guar gum), fenugreek gum, tamarind gum, cassia gum, acacia gum, gum ghatti, pectins, cellulosics, tragacanth gum, karaya gum, and combinations thereof. Non-limiting examples of suitable plant-derived mucilages include kiwi fruit mucilage (e.g., mucilage is derived from the stem pith of kiwi fruit), cactus mucilage, chia seed mucilage, psyllium mucilage, mallow mucilage, flax seed mucilage, marshmallow mucilage, ribwort mucilage, mullein mucilage, cetraria mucilage, beta-glucan and combinations thereof.

The method can comprise forming the beverage at a point of consumption by reconstituting a first powder comprising the salivating and cooling agents. The reconstituting can comprise opening a sachet containing the first powder and then combining the first powder with a liquid and a thickening agent. The combining of the first powder with the liquid and the thickening agent can comprise combining the first powder with the liquid and a second powder comprising the thickening agent.

The first powder can be an agglomerated powder further comprising a thickening agent, and the reconstituting can comprise opening a sachet containing the agglomerated powder and then combining the agglomerated powder with a liquid.

The composition can be a frozen dessert on a stick ("popsicle" in the U.S., "lolly" in the U.K.). For example, the frozen dessert can comprise the salivating agent (e.g., about 0.3 wt. % thereof), the cooling agent (e.g., about 0.04 wt. % thereof) and water (e.g., about 70-80 wt. % thereof), and optionally one or more additional ingredients comprising a stabilizer (e.g., about 0.25 wt. % thereof), a coloring agent (e.g., about 0.001 wt. % thereof), one or more sugars (e.g., about 20-25 wt. % thereof), an emulsifier (e.g., about 0.04 wt. % thereof), and a flavoring agent (e.g., about 0.25 wt. % thereof).

In another embodiment, the present disclosure provides a method of making a composition for improving hydration of an individual having dysphagia. The method comprises adding a salivating agent and a cooling agent in a weight ratio of 1:0.06 to 1:0.2 to a thickening agent.

In an embodiment, a first powder comprises the salivating and cooling agents; and the first powder is combined with the thickening agent and a liquid to form a beverage at a point of consumption.

The thickening agent can be provided by a second powder, and the adding of the salivating and cooling agents to the thickening agent can comprise adding the first powder to the second powder.

The composition can be an agglomerated powder comprising the salivating, cooling and thickening agents. The method can comprise packaging the agglomerated powder in a sachet.

In another embodiment, the present disclosure provides a method of treating dysphagia comprising administering to an individual having the dysphagia an effective amount of a composition comprising a salivating agent and a cooling agent, preferably in a weight ratio of 1:0.06 to 1:0.2. The individual can have dehydration. The individual can be at risk of dehydration, and the individual can be selected from the group consisting of elderly individuals; individuals with one or more of diabetes, dementia, fever, diarrhea, vomiting, viral gastroenteritis or bacterial gastroenteritis; individuals living at high altitudes; patient under chemotherapy or radiotherapy and combinations thereof.

In another embodiment, the present disclosure provides a ready-to-drink beverage comprising: a salivating agent and a cooling agent, preferably in a weight ratio of 1:0.06 to 1:0.2; a thickening or thin cohesive agent; and water. The ready-to-drink beverage can comprise partially hydrolyzed guar gum, for example in an amount effective to at least partially jellify the beverage.

In another embodiment, the present disclosure provides a kit for treating or preventing dehydration in an individual having impaired swallowing such as dysphagia, the kit comprising: a sachet comprising a composition comprising a salivating agent and a cooling agent and a thickening or thin cohesive agent. In a preferred embodiment the salivating and the cooling agent are in a weight ratio of 1:0.06 to 1:0.2. Preferably the thickening agent is in an additional sachet separate from the refreshing composition.

In another embodiment, the present disclosure provides a powder comprising a salivating agent and a cooling agent in a weight ratio of 1:0.06 to 1:0.2. The powder can be contained in a sachet in an amount therapeutically effective for treating or preventing dehydration in an individual having dysphagia.

An advantage of one or more embodiments provided by the present disclosure is to use an easily consumed nutritional intervention to treat dysphagia.

An additional advantage of one or more embodiments provided by the present disclosure is to improve hydration in individuals with impaired swallowing such as dysphagia.

Another advantage of one or more embodiments provided by the present disclosure is to make thickened or thin cohesive fluids more palatable and refreshing.

An additional advantage of one or more embodiments provided by the present disclosure is to decrease mortality of a dysphagia patient by treating or preventing dehydration.

Another advantage of one or more embodiments provided by the present disclosure is to deliver a measurable and tangible refreshing sensation during and after consumption of a thickened or thin cohesive beverage for dysphagic patients, comparable to the refreshing sensation induced by water, a carbonated drink, or juice.

Still another advantage of one or more embodiments provided by the present disclosure is to provide a thickened or thin cohesive beverage for dysphagic patients that supplies immediate in-mouth refreshment.

Yet another advantage of one or more embodiments provided by the present disclosure is to make saliva less viscous and sticky, thus improving the refreshing in mouth sensation and also assisting swallowing.

Additional features and advantages are described herein, and will be apparent from, the following Detailed Description.

DETAILED DESCRIPTION

All percentages expressed herein are by weight of the total weight of the composition unless expressed otherwise. When reference is made to the pH, values correspond to pH measured at 25° C. with standard equipment. All viscosities herein are values collected at 25° C. and a shear rate of 50 $s^{-1}$.

As used in this disclosure and the appended claims, the singular forms "a," "an" and "the" include plural referents unless the context clearly dictates otherwise. As used herein, "about" is understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number. All numerical ranges herein should be understood to include all integers, whole or fractions, within the range. Moreover, these numerical ranges should be construed as providing support for a claim directed to any number or subset of numbers in that range. For example, a disclosure of a range from 1 to 10 should be construed as supporting a range from 1 to 8, from 3 to 7, from 1 to 9, from 3.6 to 4.6, from 3.5 to 9.9, and so forth.

The term "and/or" used in the context of "X and/or Y" should be interpreted as "X," or "Y," or "X and Y." Where used herein, the terms "example" and "such as," particularly when followed by a listing of terms, are merely exemplary and illustrative and should not be deemed to be exclusive or comprehensive.

The compositions disclosed herein may lack any element that is not specifically disclosed herein. Thus, a disclosure of an embodiment using the term "comprising" includes a disclosure of embodiments "consisting essentially of" and "consisting of" the components identified. Similarly, the methods disclosed herein may lack any step that is not specifically disclosed herein. Thus, a disclosure of an embodiment using the term "comprising" includes a disclosure of embodiments "consisting essentially of" and "consisting of" the steps identified.

"Prevention" includes reduction of risk and/or severity of a condition or disorder. The terms "treatment," "treat" and "to alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The term does not necessarily imply that a subject is treated until total recovery. The terms "treatment" and "treat" also refer to the maintenance and/or promotion of health in an individual not suffering from a disease but who may be susceptible to the development of an unhealthy condition. The terms "treatment," "treat" and "to alleviate" are also intended to include the potentiation or otherwise enhancement of one or more primary prophylactic or therapeutic measure. The terms "treatment," "treat" and "to alleviate" are further intended to include the dietary management of a disease or condition or the dietary management for prophylaxis or prevention a disease or condition. A treatment can be patient- or doctor-related.

As used herein, an "effective amount" is an amount that prevents a deficiency, treats a disease or medical condition in an individual or, more generally, reduces symptoms, manages progression of the diseases or provides a nutritional, physiological, or medical benefit to the individual. The relative terms "improved," "increased," "enhanced" and the like refer to the effects of the composition comprising a salivating agent, a cooling agent and optionally a tingling agent (disclosed herein) relative to a composition lacking these agents but otherwise identical.

"Animal" includes, but is not limited to, mammals, which includes but is not limited to, rodents, aquatic mammals, domestic animals such as dogs and cats, farm animals such as sheep, pigs, cows and horses, and humans. Where "animal," "mammal" or a plural thereof is used, these terms also apply to any animal that is capable of the effect exhibited or intended to be exhibited by the context of the passage. As used herein, the term "patient" is understood to include an animal, especially a mammal, and more especially a human that is receiving or intended to receive treatment, as treatment is herein defined. While the terms "individual" and "patient" are often used herein to refer to a human, the present disclosure is not so limited. Accordingly, the terms "individual" and "patient" refer to any animal, mammal or human that can benefit from the treatment. In this regard, animals such as companion animals (i.e., dogs and cats) can suffer from dysphagia.

An animal is considered "elderly" if it has surpassed the first two-thirds of the average expected lifespan in its country of origin, preferably more than the first three-quarters of the average expected lifespan in its country of origin, more preferred at least the first four-fifths of the average expected lifespan in its country of origin. The term "elderly" in the context of a human means an age from birth of at least 60 years, preferably above 63 years, more preferably above 65 years. An elderly cat or dog has an age from birth of at least about 7 years.

As set forth above, the present inventors believe that a refreshing, thirst quenching solution that stimulates swallowing and salivation and increases fluid intake can avoid or mitigate dehydration in a dysphagic patient and/or treat dysphagia. Accordingly, an aspect of the present disclosure is a method comprising administering to an individual having dysphagia an effective amount of a composition comprising a salivating agent and a cooling agent in a weight ratio of 1:0.06 to 1:0.2, preferably 1:0.11 to 1:0.16. These salivating agent: cooling agent ratios provide a refreshing perception identified by physiological markers and do not impart any taste or olfactory perception, contrary to many alleged "cooling agents" which impart a taste or olfactory perception (usually a menthol-type note) and thereby limit the range of applications. In some embodiments, the composition is sugar free and comprises a sweetener (e.g., stevia).

The formulation of the composition provides a refreshing experience to support adequate fluid intake in patients with dysphagia, who rely on thickened fluids for safe swallowing. In this regard, the physiological need of a refreshing sensory experience to support hydration has an outcome of impairment that is inadequate fluid intake, and thus the composition support refreshment by including citric acid; lemon flavor; and tingling, mouth wetting and cooling flavors.

The mixture of citric acid, lemon flavor and tingling and cooling ingredients can provide a multi-sensory experience to dysphagia patients, specifically taste, aroma and trigeminal perception. This mix of ingredients has been tested in adults and demonstrated to moisten the mouth and deliver a cooling sensation, such that dysphagia patients perceive a stimulating, refreshing sensation that is well liked. Furthermore, the mixture can provide a balance of sweetness and sourness to offer a pleasurable and refreshing experience. Moreover, the combination of lemon and citric acid can deliver an intense sensation that amplifies the refreshment, such that dysphagia patients perceive a pleasurable and refreshing drinking experience that promotes good acceptance and supports adequate hydration, helping to meet their target fluid intake.

"Refreshing" sensation has been described as "a complex perception similar to the one experienced during cool water drinking, and corresponding to the relief of unpleasant physical symptoms such as elevated body temperatures or mouth dryness" (Labbe et al. 2011). Sensory properties of foods and beverages that support the delivery of a refreshing sensation have been identified, and these are reflected in the choice of ingredients for the composition.

The refreshing composition can be administered to an individual one or more times per day. In some embodiments, the composition is administered for a time period that is at least one week, preferably for at least one month; and at least one day per week, preferably at least two, three, four, five or six days per week, most preferably seven days per week.

The dysphagia can be oral pharyngeal dysphagia. In some embodiments, the dysphagia is a consequence of at least one of surgery for oral cancer, surgery for throat cancer, a stroke, a brain injury, or a progressive neuromuscular disease, such as Parkinson's disease.

The method can comprise identifying the individual as having dysphagia, e.g., before initial administration of the refreshing composition. The method can comprise identifying the dysphagic individual as having dehydration or being at risk of dehydration, e.g., before initial administration of the refreshing composition. Although dysphagic individuals are generally at risk of dehydration, some dysphagic individuals may have an even greater risk of dehydration than other dysphagic individuals. Non-limiting examples of dysphagic individuals who have a particularly increased risk of dehydration include elderly individuals; individuals with one or more of diabetes, dementia, fever (a body temperature of 38° C. or above), diarrhea, vomiting, or gastroenteritis (viral or bacterial); and individuals living at high altitudes (above about 2,500 meters), patient under chemotherapy or radiotherapy.

A salivating agent is any agent that induces salivation or a salivating reflex (e.g., mouth watering, mouth wetting or mouth hydrating). Preferably the salivating agent is one or more organic acids selected from the group consisting of adipic, ascorbic, citric, fumaric, lactic, malic and tartaric acids. These compounds stimulate salivary glands and thus enhance salivary flow.

A cooling agent is any agent that imparts a cooling sensation to the skin and mucous membranes of the body, particularly the mouth, nose, throat and gastrointestinal tract during consumption. Preferably the cooling agent is selected from the group consisting of menthol derivative compounds, acyclic and/or cyclic carboxamides, N-substituted paramenthane carboxamides, phosphine oxides, substituted p-menthanes, menthoxypropane, alpha-keto enamine derivatives, N-substituted p-menthane carboxamide, menthyl half acid ester derivatives, cubebol and mixtures thereof. In a particularly preferred embodiment, the cooling agent is a mixture comprising at least a menthol carboxamide compound.

Optionally the refreshing composition further comprises a tingling agent. A tingling agent is any agent that triggers a trigeminal perception, preferably a plant extract from pepper, onion, garlic, radish, horseradish, mustard, chili pepper or ginger. Non-limiting examples of suitable tingling agents include jambu oleoresin or para cress (*Spilanthes* sp.) in which the active ingredient is spilanthol; Japanese pepper extract (*Zanthoxylum peperitum*), such as the ingredients known as saanshool-I, saanshool-II and sanshoamide; black pepper extract (*Piper nigrum*), including the active ingredients chavicine and piperine; *Echinacea* extract; Northern Prickly Ash extract; red pepper oleoresin; and mixtures thereof.

The refreshing composition may further comprise a mixture of malic acid and citric acid to help provide an organoleptic balance between sweetness and acidity in the final product. In some embodiments, the composition further comprises a mucoadhesive agent such as hydroxypropylmethylcellulose (HPMC) and/or carboxymethylcellulose (CMC) to further enhance the salivating sensation after consumption. The composition may further comprise acidic fruity ingredients to provide fruity olfactory notes, for example pieces of acidic fruits such as citrus fruits, peach or grapefruit; the juice of such fruits; pulp of such fruits; or mixtures thereof.

The refreshing composition can further comprise any number of optional additional ingredients, including conventional food additives, for example one or more proteins, carbohydrates, fats, acidulants, thickeners, buffers or agents for pH adjustment, chelating agents, colorants, emulsifiers, excipients, flavor agents, minerals, osmotic agents, a pharmaceutically acceptable carrier, preservatives, stabilizers, sugars, sweeteners, texturizers, vitamins and/or minerals. The optional ingredients can be added in any suitable amount.

In a preferred embodiment, the refreshing composition is a powder. For example, the composition can be spray-dried, freeze-dried or subjected to any other procedure of drying known in the art. Additionally or alternatively, the composition can be made by dry mixing. Then the powder can be reconstituted with a liquid, for example water or milk, to form a refreshing beverage. The powder can be provided to the consumer in a container (e.g., a sealed container) for reconstitution in the container and/or for allowing the user to pour the powder from the container into a drinking receptacle in which the powder is reconstituted. Non-limiting examples of suitable containers include bags, boxes, cartons, bottles, or combinations thereof. Preferred containers include a sachet/stick pack, i.e., a small disposable pouch, typically of flexible film such as cellophane or paper, preferably capable of being torn open at one or both ends, and containing one serving of the composition.

In an embodiment, the beverage resulting from reconstitution of the composition comprises the salivating agent and the cooling agent in a total amount of at least 3.0 wt. %, and in some embodiments at least 6.0 wt. %. Optionally the beverage can further comprise at least 1.3 wt. % of citric acid and at least 1.0 wt. % tingling agent. In some embodiments, the beverage comprises a flavorant, such as lemon flavor and/or lemon juice flavor.

Preferably the beverage has a nectar consistency, i.e., a viscosity between 35-350 cP (e.g., 50-170 cP). In other embodiments, the viscosity is greater than 1,750 cP. In some embodiments, the beverage may be classified as Slightly Thick, Mildly Thick, Moderately Thick or Extremely thick according to the International Dysphagia Diet Standardization Initiative (IDDSI) criteria (September 2015).

In an embodiment, the consumer can add the refreshing composition to a thickening or thin cohesive agent and a liquid (e.g., water or milk) to form a beverage at the point of consumption. As used herein, "at the point of consumption" means at the same venue where the refreshing composition is administered to and/or consumed by the individual having dysphagia (e.g., a building such as a home or a care facility) and within thirty minutes before consumption, preferably within fifteen minutes before consumption, more preferably within five minutes of consumption, most preferably within one minute before consumption. In an embodiment, the individual with dysphagia can add the refreshing composition to the thickening agent and the liquid before they consume the resultant beverage. In another embodiment, another person can add the refreshing composition to the thickening agent and the liquid and then administer the resultant beverage to the individual with impaired swallowing such as dysphagia.

The manufacturer can provide a kit comprising a sachet comprising the refreshing composition comprising a salivating agent and a cooling agent, preferably in a weight ratio of 1:0.06 to 1:0.2. The kit can further comprise a thickening or thin cohesive agent, preferably in an additional sachet separate from the refreshing composition. The kit can be employed in the methods disclosed above, for example by the consumer adding the refreshing composition to the thickening or thin cohesive agent and a liquid (e.g., water or milk) to form a beverage at the point of consumption.

In an embodiment, the manufacturer can include the thickening or thin cohesive agent with the refreshing composition and thus provide an agglomerated powder. For example, the manufacturer can package an agglomerated powder comprising the refreshing composition and the thickening or thin cohesive agent in a container such as a sachet/stick pack. In such an embodiment, the beverage can be made at the point of consumption by mere addition of liquid (e.g., water or milk).

The thickening agent can be one or more of xanthan gum, guar gum (e.g., partially hydrolyzed guar gum), carrageenan, native starch, or modified starch. Additionally or alternatively, the thin cohesive agent can comprise a food grade biopolymer selected from the group consisting of botanical hydrocolloids, microbial hydrocolloids, animal hydrocolloids, algae hydrocolloids and combinations thereof. Non-limiting examples of suitable algae hydrocolloids include agar, carrageenan, alginate, and combinations thereof. Non-limiting examples of suitable microbial hydrocolloids are selected from the group consisting of xanthan gum, gellan gum, curdlan gum, and combinations thereof. Non-limiting examples of suitable botanical hydrocolloids include plant-extracted gums, plant-derived mucilages, and combinations thereof. Non-limiting examples of suitable plant-extracted gums include okra gum, konjac mannan, tara gum, locust bean gum, guar gum (e.g., partially hydrolyzed guar gum), fenugreek gum, tamarind gum, *cassia* gum, acacia gum, gum ghatti, pectins, cellulosics, tragacanth gum, karaya gum, and combinations thereof. Non-limiting examples of suitable plant-derived mucilages include kiwi fruit mucilage (e.g., mucilage is derived from the stem pith of kiwi fruit), cactus mucilage, chia seed mucilage, *psyllium* mucilage, mallow mucilage, flax seed mucilage, marshmallow mucilage, ribwort mucilage, mullein mucilage, cetraria mucilage, beta-glucan and combinations thereof.

Another embodiment of the refreshing composition is a ready-to-drink beverage. A "ready to drink" beverage is a beverage in liquid form that can be consumed without further addition of liquid. For example, the composition may be a beverage in a can or other container which may be consumed upon opening the can or container without addition of any further ingredients. In some embodiments, the beverage is a gellified water that preferably comprises partially hydrolyzed guar gum. Preferably the ready-to-drink beverage is aseptic.

Another embodiment of the refreshing composition is a frozen dessert on a stick.

Another aspect of the present disclosure is a method of making a food or beverage composition for treating impaired swallowing such as dysphagia, for example a method of enhancing the refreshment of a thickened or thin cohesive beverage. Such methods comprise adding a salivating agent and a cooling agent in a weight ratio of 1:0.06 to 1:0.2, preferably 1:0.11 to 1:0.16, to a composition comprising one or more thickening or thin cohesive agents.

The one or more thickening or thin cohesive agents can maintain elasticity and viscosity of the composition after exposure to pressure of tongue on soft and/or hard palate (e.g., xanthan), which is particularly appropriate for individuals with upper dysphagia; can lose elasticity and viscosity after exposure to pressure of tongue on soft and/or hard palate (e.g., native or modified starch from tapioca, corn, rice, other cereals, or potato), which is particularly appropriate for individuals with upper and lower dysphagia; or can maintain a minimum level of elasticity and viscosity after exposure to pressure of tongue on soft and/or hard palate (e.g., xanthan and starch/modified starch), which is particularly appropriate for individuals with upper dysphagia.

In an embodiment, the one or more thickening agents comprise carrageenan and starch. For example, the beverage can comprise about 0.03 wt. % to about 0.05 wt. % carrageenan and about 1.5 wt. % to about 4.0 wt. % starch, preferably about 0.03 wt. % to about 0.05 wt. % carrageenan and about 1.7 wt. % to about 1.9 wt. % starch, more preferably about 0.04 wt. % carrageenan and about 1.8 wt. % starch.

In an embodiment, the one or more thin cohesive agent comprise beta glucan. The composition can comprise beta-glucan in a concentration of from 0.01 wt % to 25 wt % capable of providing to the beverage: a shear viscosity of less than 200 mPas, when measured at a shear rate of 50s−1, a relaxation time, determined by a Capillary Breakup Extensional Rheometry (CaBER) experiment, of more than 10 ms (milliseconds) at a temperature of 20° C.

For flavor, a sweetener such as a sugar or sugar substitute, e.g., maltodextrin or steviol, can be included with the thickening or thin cohesive agent.

EXAMPLES

The following non-limiting examples support the concept of compositions and methods for improving hydration of individuals having dysphagia.

Example 1

The table below has two example formulations. A flavour block formulation is a lemon-flavored refreshing blend in powder form that can be provided in a sachet/stick pack. The flavour block is used at the point of consumption by addition of the powder to another powder containing a thickening agent. For reconstitution into a beverage, water is also added. Another formulation involves the thickening agent being agglomerated with the lemon-flavored refreshing blend and present together in the sachet/stick pack such that only addition to water is needed to form a beverage at the point of consumption ("all-in-one"). The beverages have a nectar consistency.

TABLE 1A

|  | Flavour block | All-in-one (agglomerated) |
| --- | --- | --- |
| Water | 1,500 g | 1,500 g |
| Thickening Agent Powder | 0 g | 18 g |
| Citric Acid 100% | 2 g | 2 g |
| Lemon Juice flavor | 1.5 g | 1.5 g |
| Tingling agent | 1.5 g | 1.5 g |
| Sweetener | 10.5 g | 10.5 g |
| Mouthwatering/cooling agent | 4.5 g | 4.5 g |

The table below has another flavour block formulation.

TABLE 1B

|  | g per Portion | g per 100 g |
| --- | --- | --- |
| Citric Acid 100% | 0.13 | 8.030 |
| Lemon flavor powder | 0.08 | 4.950 |
| Tingling agent powder | 0.1 | 6.180 |
| Cooling agent powder | 0.3 | 18.541 |
| Sweetener powder | 1.0 | 61.805 |
| Curcumin | 0.008 | 0.494 |

Example 2

The table below has a formulation that can be used to make ready-to-drink beverages that are gellified waters to be administered to and/or consumed by individuals having dysphagia.

TABLE 2A

| Ingredient | Amount |
| --- | --- |
| Potassium Chloride | 2 kg |
| Calcium Citrate | 4.2 kg |
| Xanthan and Guar Gum | 7.5 kg |
| Sweetener | 2 kg |
| Carrageenan | 110 kg |
| Anhydrous Citric Acid | 0.13 kg |
| Colorants | 1.05 kg |
| Aroma | 4.4 kg |
| Partially Hydrolyzed Guar Gum (PHGG) | 400 kg |
| Tingling agent | 10 kg |
| Mouthwatering/cooling agent | 30 kg |

The table below has another formulation that can be used to make ready-to-drink beverages that are gellified waters.

TABLE 2B

| Ingredient | Amount |
| --- | --- |
| Potassium Hydroxide | 0.0090 kg |
| Calcium Citrate | 0.0420 kg |
| Xanthan and Guar Gum | 0.0900 kg |
| Sweetener | 0.0225 kg |
| Carrageenan | 1.0000 kg |
| Cooling Agent | 0.1780 kg |
| Non-Lemon Flavor (e.g., Peach) | 0.1200 kg |
| Lemon Flavor | 0.0600 kg |
| Partially Hydrolyzed Guar Gum (PHGG) | 4.0000 kg |
| Tingling agent | 0.0560 kg |
| Colorants | 0.0075 kg |

It should be understood that various changes and modifications to the presently preferred embodiments described herein will be apparent to those skilled in the art. Such changes and modifications can be made without departing The invention is claimed as follows:

1. A method of treating or preventing dehydration in an individual having impaired swallowing, the method comprising administering to the individual an effective amount of a beverage comprising a salivating agent and a cooling agent in a total amount of at least 3.0 wt. % of the beverage, the beverage further comprising a tingling agent selected from the group consisting of spilanthol, saanshool-I, saanshool-II, sanshoamide, chavicine, piperine, *Echinacea* extract, Northern Prickly Ash extract, red pepper oleoresin, and mixtures thereof, and the individual is selected from the group consisting of individuals with one or more of fever, vomiting, or viral gastroenteritis; individuals living at high altitudes; and combinations thereof.

2. The method of claim 1 wherein the salivating agent is one or more organic acids selected from the group consisting of adipic, ascorbic, citric, fumaric, lactic, malic and tartaric acids.

3. The method of claim 1 wherein the cooling agent is selected from the group consisting of menthol compounds, acyclic carboxamides, cyclic carboxamides, N-substituted paramenthane carboxamides, phosphine oxides, substituted p-menthanes, menthoxypropane, alpha-keto enamines, N-substituted p-menthane carboxamide, menthyl half acid esters, cubebol and mixtures thereof.

4. The method of claim 1 wherein the beverage comprises a thickening agent and/or cohesive agent.

5. The method of claim 1, wherein the individual has dysphagia.

6. The method of claim 1, wherein the beverage comprises the salivating agent and the cooling agent in a total amount of at least 6.0 wt. % of the beverage.

7. The method of claim 1, wherein the beverage has a viscosity of 35-350 cP.

8. The method of claim 1, wherein the beverage has a viscosity greater than 1,750 cP.

9. The method of claim 1, wherein the beverage comprises a food grade biopolymer selected from the group consisting of botanical hydrocolloids, microbial hydrocolloids, animal hydrocolloids, algae hydrocolloids, and combinations thereof.

10. A method of treating or preventing dehydration in an individual having dysphagia, the method comprising administering to the individual an effective amount of a beverage comprising a salivating agent and a cooling agent in a weight ratio of 1:0.06 to 1:0.2 and a total amount of at least 3.0 wt. % of the beverage, the beverage further comprising a tingling agent selected from the group consisting of spilanthol, saanshool-I, saanshool-II, sanshoamide, chavicine, piperine, *Echinacea* extract, Northern Prickly Ash extract, red pepper oleoresin, and mixtures thereof, and the individual is selected from the group consisting of individuals with one or more of fever, vomiting, or viral gastroenteritis; individuals living at high altitudes; and combinations thereof.

11. The method of claim 10 wherein the salivating agent is one or more organic acids selected from the group consisting of adipic, ascorbic, citric, fumaric, lactic, malic and tartaric acids.

12. The method of claim 10 wherein the cooling agent is selected from the group consisting of menthol compounds, acyclic carboxamides, cyclic carboxamides, N-substituted paramenthane carboxamides, phosphine oxides, substituted p-menthanes, menthoxypropane, alpha-keto enamines, N-substituted p-menthane carboxamide, menthyl half acid esters, cubebol and mixtures thereof.

13. The method of claim 10 wherein the beverage comprises a thickening agent and/or cohesive agent.

14. The method of claim 10, wherein the beverage comprises the salivating agent and the cooling agent in a total amount of at least 6.0 wt. % of the beverage.

15. A method of treating impaired swallowing in an individual having dysphagia, the method comprising administering to the individual an effective amount of a beverage comprising a salivating agent and a cooling agent in a weight ratio of 1:0.06 to 1:0.2 and a total amount of at least 3.0 wt. % of the beverage, the beverage further comprising a tingling agent selected from the group consisting of spilanthol, saanshool-I, saanshool-II, sanshoamide, chavicine, piperine, *Echinacea* extract, Northern Prickly Ash extract, red pepper oleoresin, and mixtures thereof, and the individual is selected from the group consisting of individuals with one or more of fever, vomiting, or viral gastroenteritis; individuals living at high altitudes; and combinations thereof.

16. The method of claim 15 wherein the individual has dehydration.

17. The method of claim 15 wherein the individual is at risk of dehydration.

18. The method of claim 15, wherein the beverage comprises the salivating agent and the cooling agent in a total amount of at least 6.0 wt. % of the beverage.

* * * * *